(12) United States Patent
Heersink et al.

(10) Patent No.: US 11,564,965 B2
(45) Date of Patent: Jan. 31, 2023

(54) **COMPOSITIONS FOR THE TREATMENT OF *DEMODEX BLEPHARITIS*, ACNE AND JOINT PAIN**

(71) Applicant: Lunovus LLC, Birmingham, AL (US)

(72) Inventors: Marnix Heersink, Dothan, AL (US); Sebastian Heersink, Dothan, AL (US); Marius Heersink, Dothan, AL (US); Don Johnson, Birmingham, AL (US)

(73) Assignee: Lunovus LLC, Birmingham, AL (US)

( * ) Notice: Subject to any disclaimer, the term of this patent is extended or adjusted under 35 U.S.C. 154(b) by 186 days.

(21) Appl. No.: 16/912,996

(22) Filed: Jun. 26, 2020

(65) Prior Publication Data

US 2021/0401920 A1 Dec. 30, 2021

(51) Int. Cl.
| | | |
|---|---|---|
| *A61K 36/61* | (2006.01) |
| *A61K 36/889* | (2006.01) |
| *A61K 36/886* | (2006.01) |
| *A61K 47/10* | (2017.01) |
| *A61K 47/14* | (2017.01) |
| *A61K 47/18* | (2017.01) |
| *A61K 47/26* | (2006.01) |
| *A61K 47/02* | (2006.01) |
| *A61K 47/20* | (2006.01) |
| *A61K 35/644* | (2015.01) |

(52) U.S. Cl.
CPC ............ *A61K 36/61* (2013.01); *A61K 35/644* (2013.01); *A61K 36/886* (2013.01); *A61K 36/889* (2013.01); *A61K 47/02* (2013.01); *A61K 47/10* (2013.01); *A61K 47/14* (2013.01); *A61K 47/183* (2013.01); *A61K 47/20* (2013.01); *A61K 47/26* (2013.01)

(58) Field of Classification Search
CPC .... A61K 36/61; A61K 35/644; A61K 36/886; A61K 36/889; A61K 47/02; A61K 47/10; A61K 47/14; A61K 47/183; A61K 47/20; A61K 47/26; A61K 9/0014; A61K 47/44
See application file for complete search history.

(56) References Cited

U.S. PATENT DOCUMENTS

| | | | | |
|---|---|---|---|---|
| 2006/0210516 | A1* | 9/2006 | Mower | A61Q 17/04 424/70.13 |
| 2015/0044157 | A1* | 2/2015 | Kulkarni | A61K 8/602 514/561 |
| 2019/0117563 | A1* | 4/2019 | McAnnally | A61K 36/889 |

FOREIGN PATENT DOCUMENTS

| | | | | |
|---|---|---|---|---|
| CA | 2894002 A1 * | 6/2014 | | A61K 31/555 |
| WO | WO-2019136105 A1 * | 7/2019 | | A61K 36/18 |

OTHER PUBLICATIONS

Wang (CN108524711A Machine English Translation) (Year: 2018).*

* cited by examiner

*Primary Examiner* — Robert A Wax
*Assistant Examiner* — Quanglong N Truong
(74) *Attorney, Agent, or Firm* — Burr & Forman LLP; Harvey S. Kauget

(57) ABSTRACT

A composition for the treatment of *Demodex blepharitis* and/or acne containing tea tree oil (TTO), coconut oil, aloe barbadensis, decyl glucoside, sodium chloride, sodium lauroyl methyl isethionate, Caprylic/Capric Triglyceride, Caprylyl Glycol, Ethylhexylglycerin, and Hexylene Glycol in glycerin or in water or in a mixture of glycerin and water. The composition is used to treat *Demodex blepharitis* and/or acne by applying the composition to the eyelid margin and eyelashes or acne and scrubbing the eyelid margin, eyelashes, and eyelash roots or acne with the composition using any suitable cloth, wipe, sponge, brush, or cotton tipped applicator.

2 Claims, No Drawings

COMPOSITIONS FOR THE TREATMENT OF *DEMODEX BLEPHARITIS*, ACNE AND JOINT PAIN

TECHNICAL FIELD

The present invention relates to methods and compositions for treating ocular *Demodex, Demodex*-induced *blepharitis* and/or acne using tea tree oil in combination with coconut oil. The present invention also relates to methods and compositions for treating joint pain using Cannabidiol (CBD) oil.

BACKGROUND ART

*Demodex* (class Arachnida, superorder Acariformes) is one of the most commonly found ectoparasites in humans. On the eyelids, *D. folliculorum* lives in the eyelash follicles and *D. brevis* lives deep in the meibomian glands and the sebaceous glands of the lashes. They eat skin cells, and oils in the hair follicle. It is reported that *Demodex* is an etiologic factor in chronic *blepharitis*, conjunctival inflammation, and meibomian gland dysfunction. Patients who suffer from *blepharitis* as a result of an ocular *Demodex* infestation often present a number of symptoms such as foreign body sensation in the eye, redness, and itching. Uncontrolled ocular *Demodex* infestation in eyelids may cause mal-directed eye lashes (trichiasis), meibomian gland dysfunction leading to lipid tear deficient dry eye, conjunctival inflammation (conjunctivitis), and sight-threatening corneal abnormalities. The symptoms can become severe enough that the patient may require surgery to achieve relief.

Tea tree oil (TTO) is natural oil distilled from the leaf of *Melaleuca alternifolia*. TTO is known to be effective for killing *Demodex* in vitro and in vivo. A lid scrubbing treatment with TTO is known to be effective for decreasing *Demodex* in eyelashes treated with a cotton tip wetted with 10% TTO (Koo et al, J Korean Med Sci 2012; 27: 1574-1579). One of the active components of TTO is terpinen-4-ol. U.S. Pat. No. 8,455,015 discloses that terpinen-4-ol is effective in treating an ocular *Demodex* infestation or *Demodex*-induced *blepharitis* in the form of solutions, suspensions, sprays, lotions, gels, pastes, medicated sticks, balms, cleansers (including shampoos and soaps), creams, or ointments. In addition, various studies show that tea tree oil is just as effective as some of the commonly used dermatological cures for acne. According to research, tea-tree oil is rich in terpinene-4-ol, which makes it significantly more effective in treating acne than commercial options like benzoyl peroxide. Terpinene-4-ol causes antimicrobial activity, and this destroys the skin-based bacteria responsible for acne.

Cannabidiol (CBD) is a type of cannabinoid, a chemical found naturally in cannabis (marijuana and hemp) plants. Studies have shown that CBD can be an effective therapeutic aid for pain that is associated with arthritis. Generally, CBD has strong anti-inflammatory properties and studies suggest that it can be used to reduce the inflammation and pain that is associated with different types of arthritis.

DISCLOSURE OF THE INVENTION

In one embodiment of the present invention, a composition is provided for the treatment of *Demodex blepharitis* and/or acne containing tea tree oil (TTO), 0.1 to 10% v/v, and/or coconut oil, 0.1 to 10% v/v, in glycerin or in water or in a mixture of glycerin and water. The composition may further contain aloe barbadensis gel, 0.1 to 10% v/v, PEG-40 hydrogenated castor oil, 0.1 to 10% v/v, sodium phytate, 0.1 to 10% v/v, decyl glucoside, 0.1 to 10% v/v, cocamidopropyl betaine, 0.1 to 10% v/v, sodium chloride, 0.1 to 10% v/v, sodium lauroyl methyl isethionate, 0.1% to 10% v/v, caprylic/capric triglyceride, 0.1 to 10% v/v, phenoxyethanol, 0.1 to 10% v/v, caprylyl glycol, 0.1 to 10% v/v, ethylhexylglycerin, 0.1 to 10% v/v, or hexylene Glycol, 0.1 to 10% v/v, or a combination thereof, in glycerin or in water or in a mixture of glycerin and water.

In another embodiment of the present invention, a composition is provided for the treatment of *Demodex blepharitis* and/or acne containing tea tree oil (TTO), 0.1 to 10% v/v, and/or coconut oil, 0.1 to 10% v/v, in glycerin or in water or in a mixture of glycerin and water. The composition may further contain aloe barbadensis gel, 0.1 to 10% v/v, sodium lauroyl methyl isethionate, 0.1% to 1% v/v, decyl glucoside, 0.1 to 10% v/v, cocamidopropyl betaine, 0.1 to 10% v/v, sodium chloride, 0.1 to 10% v/v, caprylic/capric triglyceride, 0.1 to 10% v/v, polysorbate 20, 0.1 to 10% v/v, phenoxyethanol, 0.1 to 10% v/v, caprylyl glycol, 0.1 to 10% v/v, ethylhexylglycerin, 0.1 to 10% v/v, hexylene Glycol, 0.1 to 10% v/v, or disodium EDTA, 0.1 to 10% v/v, or a combination thereof, in glycerin or in water or in a mixture of glycerin and water.

In another embodiment of the present invention, a composition is provided for the treatment of *Demodex blepharitis* and/or acne containing tea tree oil (TTO), 0.1 to 10% v/v, and/or coconut oil, 0.1 to 10% v/v, in glycerin or in water or in a mixture of glycerin and water. The composition may further contain aloe barbadensis gel, 0.1 to 10% v/v, PEG-40 hydrogenated castor oil, 0.1 to 10% v/v, honey (Mel), 0.1 to 10% v/v, sodium phytate, 0.1 to 10% v/v, decyl glucoside, 0.1 to 10% v/v, cocamidopropyl betaine, 0.1 to 10% v/v, sodium chloride, 0.1 to 10% v/v, sodium lauroyl methyl isethionate, 0.1% to 10% v/v, caprylic/capric triglyceride, 0.1 to 10% v/v, phenoxyethanol, 0.1 to 10% v/v, caprylyl glycol, 0.1 to 10% v/v, ethylhexylglycerin, 0.1 to 10% v/v, hexylene Glycol, 0.1 to 10% v/v, trisodium ethylenediamine disuccinate, 0.1 to 10% v/v, or sodium benzoate, 0.1 to 10% v/v, or a combination thereof, in glycerin or in water or in a mixture of glycerin and water.

In another embodiment of the present invention, a composition is provided for the treatment of *Demodex blepharitis* and/or acne containing tea tree oil (TTO), 0.1 to 10% v/v, and/or coconut oil, 0.1 to 10% v/v. The composition may further contain PEG-8, 0.1 to 10% v/v, PEG-4, 0.1 to 10% v/v, PVP, 0.1 to 10% v/v, phenoxyethanol, 0.1 to 10% v/v, or ethylhexylglycerin, 0.1 to 10% v/v, or a combination thereof, in glycerin or in water or in a mixture of glycerin and water.

This invention further provides a method for treating *Demodex blepharitis* and/or acne. The compositions described herein are provided to a subject having *Demodex blepharitis* and/or acne. The composition is applied to the eyelid margin and eyelashes and/or acne. The eyelid margin, eyelashes, and eyelash roots and/or acne are scrubbed with the composition. Any suitable cloth, wipe, sponge, brush, or cotton tipped applicator may be used for scrubbing.

In another embodiment of the present invention, a composition is provided for the treatment of joint pain containing Cannabidiol (CBD) oil, 0.1 to 10% v/v, and/or coconut oil, 0.1 to 10% v/v, in glycerin or in water or in a mixture of glycerin and water. The composition may further contain polysorbate 20, 0.1 to 10% v/v, aloe barbadensis gel, 0.1 to 10% v/v, sodium phytate, 0.1% to 1% v/v, decyl glucoside, 0.1 to 10% v/v, cocamidopropyl betaine, 0.1 to 10% v/v, sodium chloride, 0.1 to 10% v/v, sodium lauroyl methyl isethionate, 0.1% to 1% v/v, caprylic/capric triglyceride, 0.1 to 10% v/v, trisodium ethylenediamine disuccinate, 0.1 to 10% v/v, phenoxyethanol, 0.1 to 10% v/v, caprylyl glycol, 0.1 to 10% v/v, ethylhexylglycerin, 0.1 to 10% v/v, hexylene Glycol, 0.1 to 10% v/v, or sodium benzoate, 0.1 to 10% v/v, or a combination thereof, in glycerin or in water or in a mixture of glycerin and water.

BEST MODES FOR CARRYING OUT THE INVENTION

While the following description details the preferred embodiments of the present invention, it is to be understood that the invention is not limited in its application to the details of the disclosures and descriptions in the accompanying specification, since the invention is capable of other embodiments and of being practiced in various ways.

The present invention provides an increased, improved effectiveness of tea tree oil (TTO) for treating *Demodex blepharitis* and/or acne by combining TTO with coconut oil. Coconut oil is active as an anti-microbial and moisturizer. Addition of other key ingredients can further improve the effectiveness of tea tree TTO for treating *Demodex blepharitis* and/or acne.

In one embodiment for use as a cleanser, TTO is formulated at 0.1 to 10%, preferably 1%, v/v, and coconut oil is formulated at 0.1 to 10%, preferably 1%, v/v, in substances such as glycerin or water or a mixture of glycerin and water. Other ingredients that can be combined with TTO and/or coconut oil are aloe barbadensis gel, 0.1 to 1% v/v; PEG-40 hydrogenated castor oil, 0.1 to 1% v/v, sodium phytate, 0.1 to 1% v/v, decyl glucoside, 0.1 to 1% v/v, cocamidopropyl betaine, 0.1 to 1% v/v, sodium chloride, 0.1 to 1% v/v, sodium lauroyl methyl isethionate, 0.1% to 1% v/v, caprylic/capric triglyceride, 0.1 to 1% v/v, phenoxyethanol, 0.1 to 1% v/v, caprylyl glycol, 0.1 to 1% v/v, ethylhexylglycerin, 0.1 to 1% v/v, or hexylene Glycol, 0.1 to 1% v/v.

In one embodiment for use as a foaming bottle solution, TTO is formulated at 0.1 to 10%, preferably 1%, v/v, and coconut oil is formulated at 0.1 to 10%, preferably 1%, v/v, in substances such as glycerin or water or a mixture of glycerin and water. Other ingredients that can be combined with TTO and/or coconut oil are aloe barbadensis gel, 0.1 to 10% v/v, sodium lauroyl methyl isethionate, 0.1% to 1% v/v, decyl glucoside, 0.1 to 10% v/v, cocamidopropyl betaine, 0.1 to 10% v/v, sodium chloride, 0.1 to 10% v/v, caprylic/capric triglyceride, 0.1 to 10% v/v, polysorbate 20, 0.1 to 10% v/v, phenoxyethanol, 0.1 to 10% v/v, caprylyl glycol, 0.1 to 10% v/v, ethylhexylglycerin, 0.1 to 10% v/v, hexylene Glycol, 0.1 to 10% v/v, or disodium EDTA, 0.1 to 10% v/v, or a combination thereof, in glycerin or in water or in a mixture of glycerin and water.

In one embodiment for use as a cleanser with honey, TTO is formulated at 0.1 to 10%, preferably 1%, v/v, and coconut oil is formulated at 0.1 to 10%, preferably 1%, v/v, in substances such as glycerin or water or a mixture of glycerin and water. Other ingredients that can be combined with TTO and/or coconut oil are aloe barbadensis gel, 0.1 to 10% v/v, PEG-40 hydrogenated castor oil, 0.1 to 10% v/v, honey (Mel), 0.1 to 10% v/v, sodium phytate, 0.1 to 10% v/v, decyl glucoside, 0.1 to 10% v/v, cocamidopropyl betaine, 0.1 to 10% v/v, sodium chloride, 0.1 to 10% v/v, sodium lauroyl methyl isethionate, 0.1% to 10% v/v, caprylic/capric triglyceride, 0.1 to 10% v/v, phenoxyethanol, 0.1 to 10% v/v, caprylyl glycol, 0.1 to 10% v/v, ethylhexylglycerin, 0.1 to 10% v/v, hexylene Glycol, 0.1 to 10% v/v, trisodium ethylenediamine disuccinate, 0.1 to 10% v/v, or sodium benzoate, 0.1 to 10% v/v, or a combination thereof, in glycerin or in water or in a mixture of glycerin and water.

In one embodiment for use as a warming solution, TTO is formulated at 0.1 to 10%, preferably 1%, v/v, and coconut oil is formulated at 0.1 to 10%, preferably 1%, v/v, in substances such as glycerin or water or a mixture of glycerin and water. Other ingredients that can be combined with TTO and/or coconut oil are PEG-8, 0.1 to 10% v/v, PEG-4, 0.1 to 10% v/v, PVP, 0.1 to 10% v/v, phenoxyethanol, 0.1 to 10% v/v, or ethylhexylglycerin, 0.1 to 10% v/v, or a combination thereof, in glycerin or in water or in a mixture of glycerin and water.

In one embodiment for use as a pain relief solution, Cannabidiol (CBD) oil is formulated at 0.1 to 10%, preferably 1%, v/v, and coconut oil is formulated at 0.1 to 10%, preferably 1%, v/v, in substances such as glycerin or water or a mixture of glycerin and water. Other ingredients that can be combined with CBD oil and/or coconut oil are polysorbate 20, 0.1 to 10% v/v, aloe barbadensis gel, 0.1 to 10% v/v, sodium phytate, 0.1% to 1% v/v, decyl glucoside, 0.1 to 10% v/v, cocamidopropyl betaine, 0.1 to 10% v/v, sodium chloride, 0.1 to 10% v/v, sodium lauroyl methyl isethionate, 0.1% to 1% v/v, caprylic/capric triglyceride, 0.1 to 10% v/v, trisodium ethylenediamine disuccinate, 0.1 to 10% v/v, phenoxyethanol, 0.1 to 10% v/v, caprylyl glycol, 0.1 to 10% v/v, ethylhexylglycerin, 0.1 to 10% v/v, hexylene Glycol, 0.1 to 10% v/v, or sodium benzoate, 0.1 to 10% v/v, or a combination thereof, in glycerin or in water or in a mixture of glycerin and water.

Formulations and compositions of TTO and/or coconut oil can be used in combination with cleaning towels or cotton tipped applicators for application of the formulation to the eyelid and/or acne. The formulations and compositions can also be prepared in a foam dispensing bottle having a pharmaceutical foam composition comprising water, a hydrophobic solvent, a surface-active agent, or a gelling agent, or a combination thereof, and a propellant.

The formulations and compositions of TTO and/or coconut oil provide a method of treating an ocular *Demodex*-induced *blepharitis* in the eyelid and/or acne. The method includes administering to the eyelid and/or acne a therapeutically-effective amount of a composition having TTO and coconut oil as active agents. The composition is administered topically to the eyelid margin and eyelashes and/or acne by means of a cleaning towel, a cotton tip applicator, or a foam composition, or a combination thereof. The eyelid margin, eyelashes, and eyelash roots and/or acne are scrubbed with the composition.

Any of the compositions described herein are provided to a person having *Demodex*-induced *blepharitis* in the eyelid and/or acne. The composition is applied to the eyelid margin and eyelashes and/or acne. The eyelid margin, eyelashes, and eyelash roots and/or acne are scrubbed with the composition using any suitable cloth, wipe, sponge, brush, or cotton tipped applicator.

Any of the compositions described herein containing Cannabidiol (CBD) oil are provided to a person having joint pain. The composition is applied to the affected joint. The affected joint is scrubbed with the composition using any suitable cloth, wipe, sponge, brush, or cotton tipped applicator.

While this invention has been described in some detail with reference to specific exemplary embodiments, there is no intention that the invention be limited to such detail. On the contrary, the invention is intended to include any alternative or equivalent embodiments that fall within the spirit and scope of the invention as described and claimed herein.

The invention claimed is:

1. A composition in glycerin or in water or in a mixture of glycerin and water for the treatment of *Demodex blepharitis* or acne, consisting of: tea tree oil (TTO), 0.1 to 10% v/v; coconut oil in an amount less than 1% v/v; aloe barbadensis, 0.1 to 10% v/v; PEG-40 hydrogenated castor oil, 0.1 to 10% v/v; sodium phytate, 0.1 to 10% v/v; decyl glucoside, 0.1 to 10% v/v; cocamidopropyl betaine, 0.1 to 10% v/v; sodium chloride, 0.1 to 10% v/v; sodium lauroyl methyl isethionate, 0.1% to 10% v/v; caprylic/capric triglyceride, 0.1 to 10% v/v; phenoxyethanol, 0.1 to 10% v/v; caprylyl glycol, 0.1 to 10% v/v; ethylhexylglycerin, 0.1 to 10% v/v; and hexylene Glycol, 0.1 to 10% v/v.

2. A composition in glycerin or in water or in a mixture of glycerin and water for the treatment of *Demodex blepharitis* or acne, consisting of: tea tree oil (TTO), 0.1 to 10% v/v; coconut oil in an amount less than 1% v/v; aloe barbadensis, 0.1 to 10% v/v; sodium lauroyl methyl isethionate, 0.1% to 1% v/v; decyl glucoside, 0.1 to 10% v/v; cocamidopropyl betaine, 0.1 to 10% v/v; sodium chloride, 0.1 to 10% v/v; caprylic/capric triglyceride, 0.1 to 10% v/v; polysorbate 20, 0.1 to 10% v/v; phenoxyethanol, 0.1 to 10% v/v; caprylyl glycol, 0.1 to 10% v/v; ethylhexylglycerin, 0.1 to 10% v/v; hexylene Glycol, 0.1 to 10% v/v and disodium EDTA, 0.1 to 10% v/v.

* * * * *